US00PP21299P3

(12) United States Plant Patent
Pringle

(10) Patent No.: US PP21,299 P3
(45) Date of Patent: Sep. 21, 2010

(54) TAMARILLO PLANT NAMED 'SWEETEN'

(50) Latin Name: *Cyphomandra betacea*
Varietal Denomination: Sweeten

(75) Inventor: Greg Pringle, Auckland (NZ)

(73) Assignee: The Horticulture & Food Research Institute of New Zealand Limited, Auckland (NZ)

( * ) Notice: Subject to any disclaimer, the term of this patent is extended or adjusted under 35 U.S.C. 154(b) by 227 days.

(21) Appl. No.: 12/283,005

(22) Filed: Sep. 9, 2008

(65) Prior Publication Data

US 2010/0064398 P1 Mar. 11, 2010

(51) Int. Cl.
*A01H 5/00* (2006.01)

(52) U.S. Cl. ..... Plt./156

(58) Field of Classification Search ..... Plt./156
See application file for complete search history.

*Primary Examiner*—Wendy C. Haas
(74) *Attorney, Agent, or Firm*—Greenlee Winner and Sullivan, P.C.

(57) ABSTRACT

A new and distinct tamarillo variety is described. The variety results from selection among a population of seedlings derived from hybridization among red, amber, and yellow-fruited tamarillo selections. This new variety is characterized by bright red skin color and sweet flavor. The new variety appears suitable for the fresh fruit market and has been named 'Sweeten'.

14 Drawing Sheets

Genus and species of plant claimed: *Cyphomandra betacea.*

Variety denomination: 'Sweeten'.

BACKGROUND OF THE INVENTION

The invention relates to a tamarillo (*Cyphomandra betacea*) tree bearing fruit suitable for the fresh fruit market.

The tree tomato, renamed the tamarillo in New Zealand around 1970, under cultivation produces an edible fruit, similar in size and shape to a hen egg. Generally believed to be native to the Andean region of Peru, and extending in range into Chile, Ecuador, and Bolivia, it is cultivated in Argentina, Brazil, Colombia, and Venezuela.

Grown in New Zealand both as a commercial crop and by amateur growers, seed is thought to have been first introduced in the late 1800's, obtained from a missionary in Ecuador. In the wild, the fruit is generally small, splotchy and yellow or pale red in color. Selection and improvement by nurserymen have resulted in large red-fruited strains. Golden cultivars, ranging yellow to amber in external coloration, have also been introduced.

The tamarillo is a member of the Solanaceae family. It is a subtropical rather than tropical plant, and while succeeding in cooler climates, does best where the temperature remains above 10° C. Tamarillos are rapidly growing trees which produce good crops after 18 months. They are frost tender, seedlings and cuttings being most vulnerable in their first year, more mature plants tending to recover after frost damage so long as it is not too severe or prolonged.

Fruit are highly attractive and are usually cut and eaten with a spoon. Some people find the skin astringent and flesh too acid to their taste. However, the flavor overall is sweet to sub-acid, and the pulp juicy. Tamarillos are considered a nutritious fruit containing good quantities of several important vitamins including A, B6, C and E, are rich in iron and potassium, low in sodium, and a good source of fibre. While an excellent fruit for fresh consumption it has a limited storage life, suffering from chilling injury and post-harvest pathogens if maintained below 5° C. for any sustained period of time. Fruit processes extremely well, especially as pulp, puree, and juice.

SUMMARY OF THE INVENTION

The new variety was selected from a population of seedlings derived from conventional hybridization among unpatented red, amber, and yellow-fruited tamarillo germplasm available in New Zealand. The objective of the crossing program was to produce a variety with sweeter fruit than was typically available, and suitable for commercial fruit production. The new variety was selected in the 1993-94 fruiting season from among seedlings located on land controlled by the Horticulture and Food Research Institute of New Zealand Limited at Northland, New Zealand, and was assigned the breeder code, 4G3. The new variety has since been named 'Sweeten'. The parents of the new variety are not known. The new variety differed from the possible parent varieties by having a combination of bright red fruit skin colour and sweet flavor.

The original selection was asexually propagated as hardwood cuttings over the next twelve years. Throughout this time the plants were observed to be true to the original parent plant. The characteristics of the new variety are stable and transmitted without change through succeeding generations.

BRIEF DESCRIPTION OF THE PHOTOGRAPHS

The accompanying photographs show typical specimens of the plant, foliage and fruit of the new variety as depicted in colors as nearly true as is reasonably possible to make the same in a color illustration of this character.

DETAILED BOTANICAL DESCRIPTION

Horticultural terminology is used in accordance with UPOV guidelines. All dimensions in millimeters, weights in grams (unless otherwise stated). Where a color reference is given these refer to The R.H.S. Colour Chart, The Royal Horticultural Society, London. 4$^{th}$ Edition, 2001. The specimens described were grown at Kerikeri, Northland, New Zealand.

Published environmental data relating to growing conditions for Northland, New Zealand is as follows (based on mean annual values 1971-2000):

- Rainfall 1671 mm
- Sunshine hours 1964
- Ground frost 12 days
- Heat units 1912 degree days

PLANT DESCRIPTION

Figure 1:
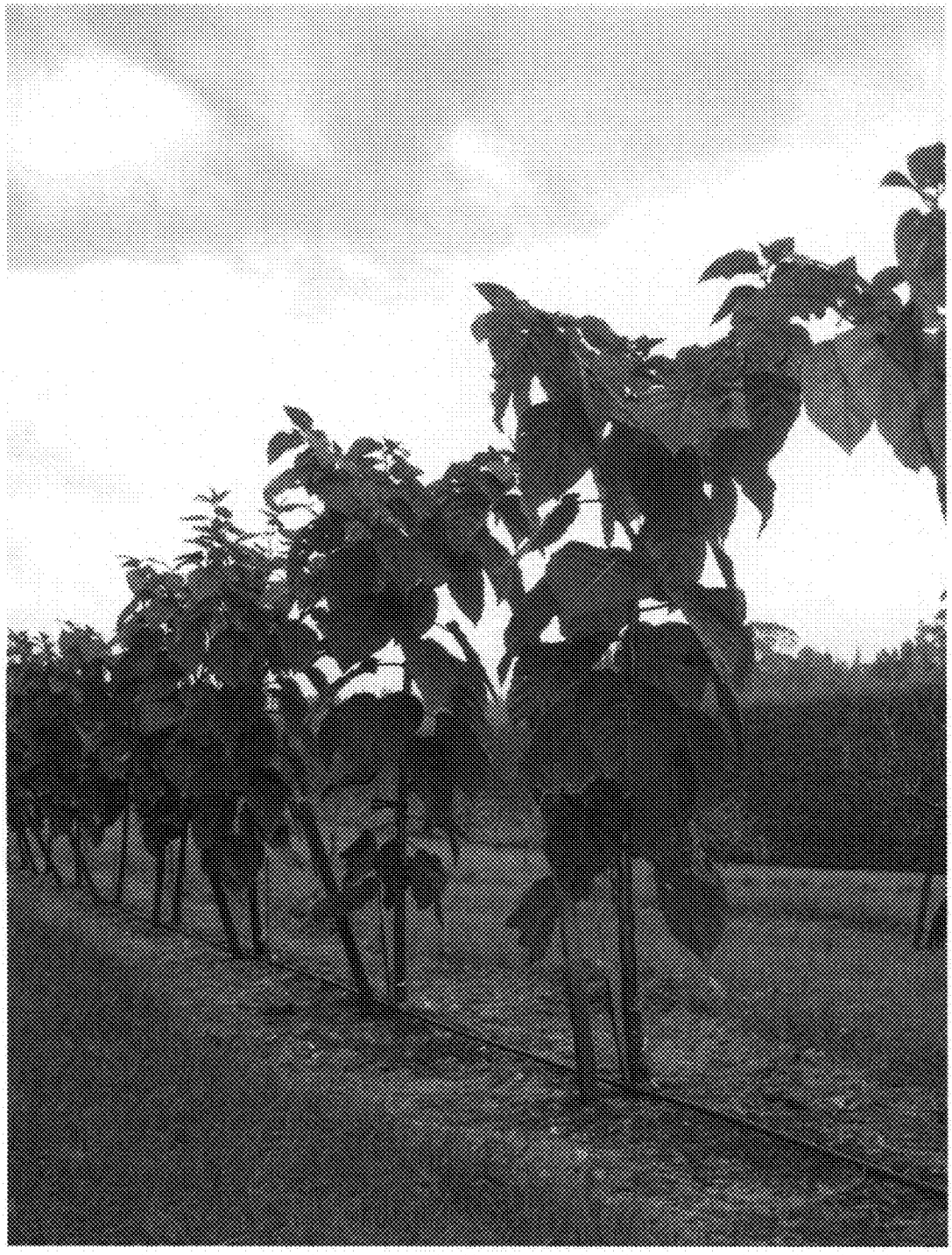
FIG. 1 shows a young tree of the variety 'Sweeten' in an orchard.
Figure 2:
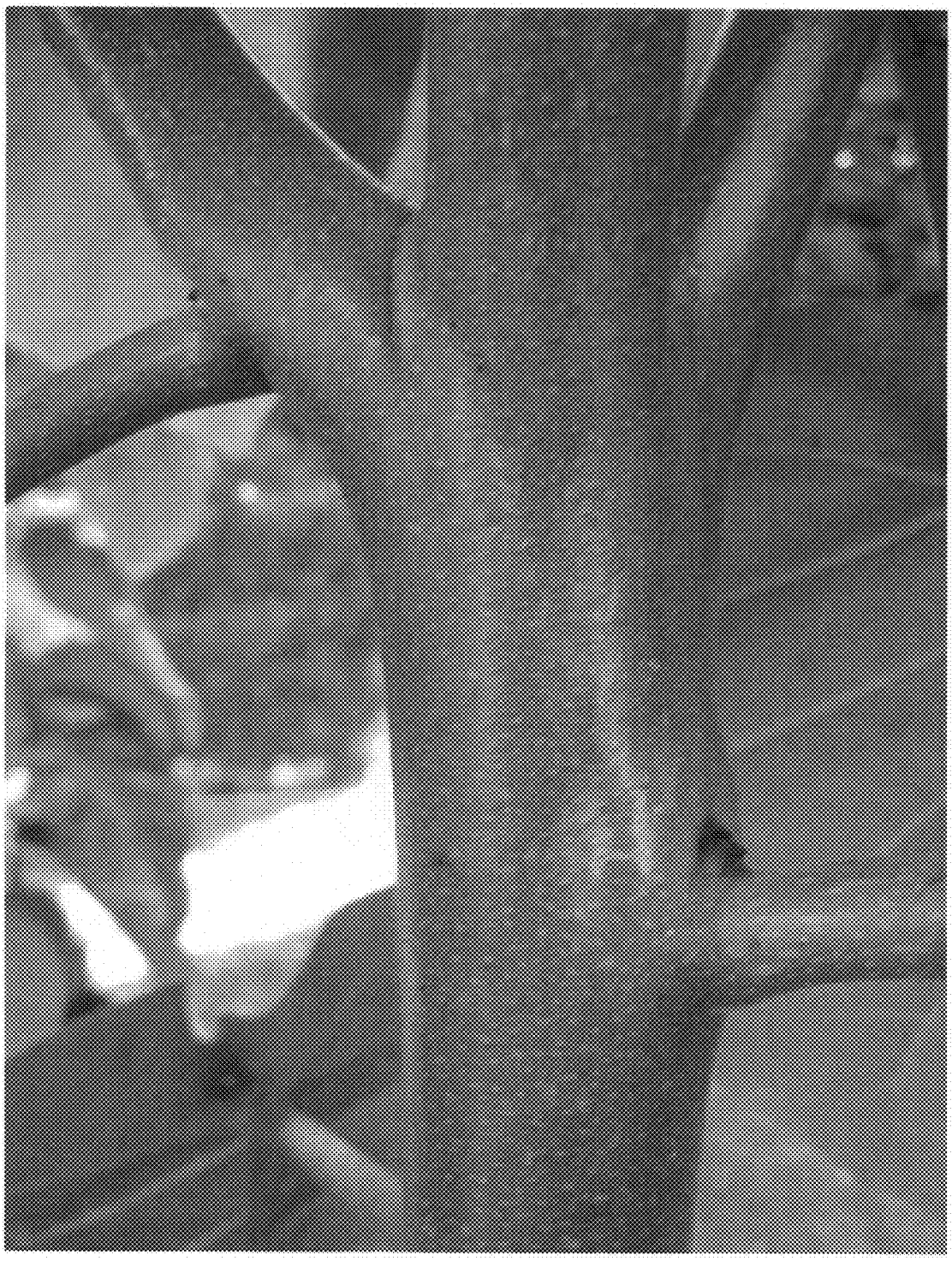
FIG. 2 shows an example of the main trunk of the plant of the variety 'Sweeten'.
Figure 3:
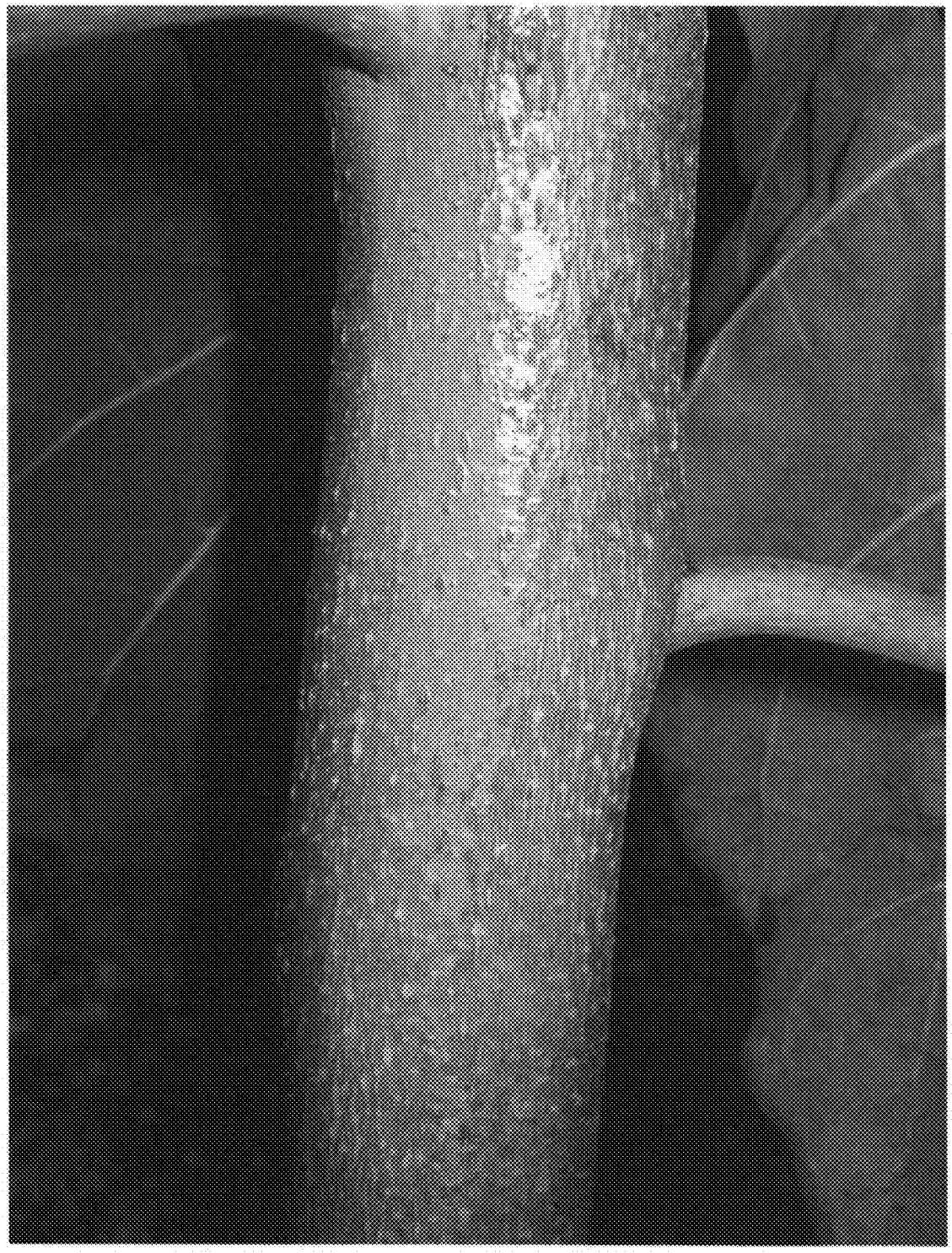
FIG. 3 shows an example of a mature, and slightly woody, section the main trunk of the plant of the variety 'Sweeten'.

Plant and foliage: A small semi-woody, evergreen, tree with a short stem with a crown of divergent branches. The plant exhibits an overall upright growth habit with medium vigor (FIG. 1). It is shallow-rooted, with a fine fibrous root system. Mature plant height is commonly in the range 3000 mm to 5500 mm, although this may vary with the growing conditions. The main trunk of the plant is typically green (near Green 143C) in color (FIG. 2). Many light colored lenticels are evident (near Green 142D in color) (FIG. 2). The most mature sections, typically near the base of the trunk, tend to more brown in color (near Greyed-orange 175A and 175C), and appear more woody (FIG. 3). The trunk is smooth. The plant is multi-branched, the main branches arising from the central stem typically at about 160 cm from ground level. The branching pattern is highly influenced by the terminal flowering habit; the occurrence of a terminal inflorescence causing the buds of two subtending leaves to break and form shoots. No pubescence is evident on the trunk, branches, or other stems.

Figure 4:
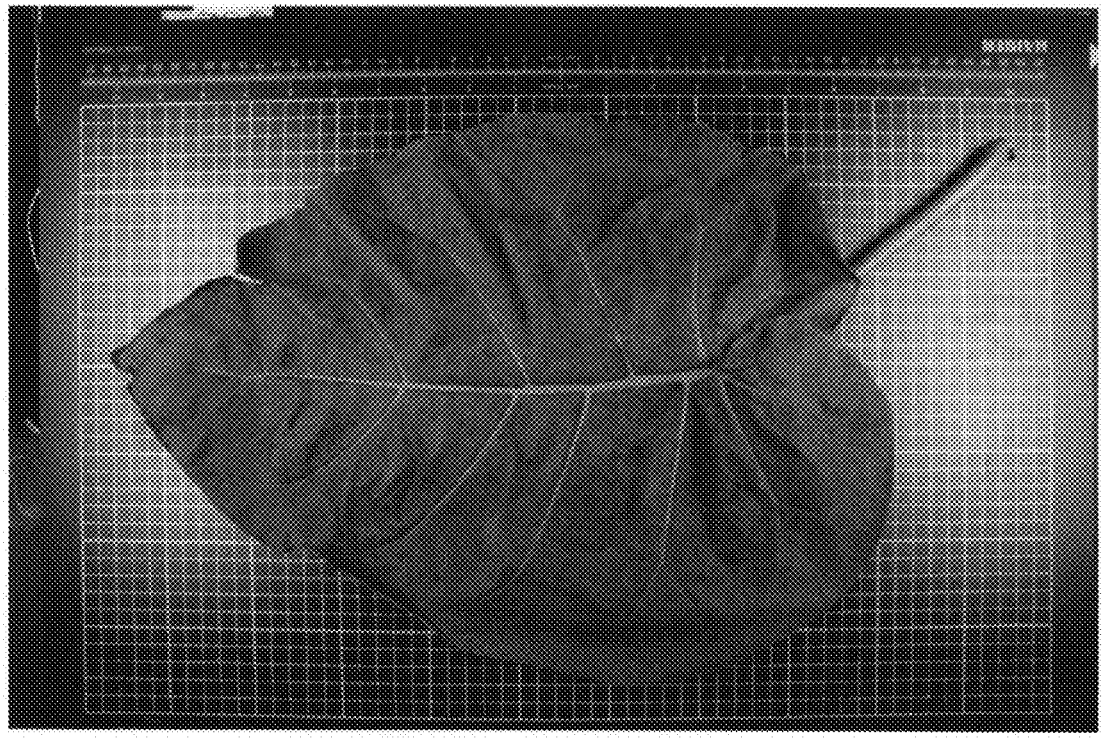
FIG. 4 shows an example of a mature leaf of the plant of the variety 'Sweeten'; view is of the upper surface of the leaf.
Figure 5:
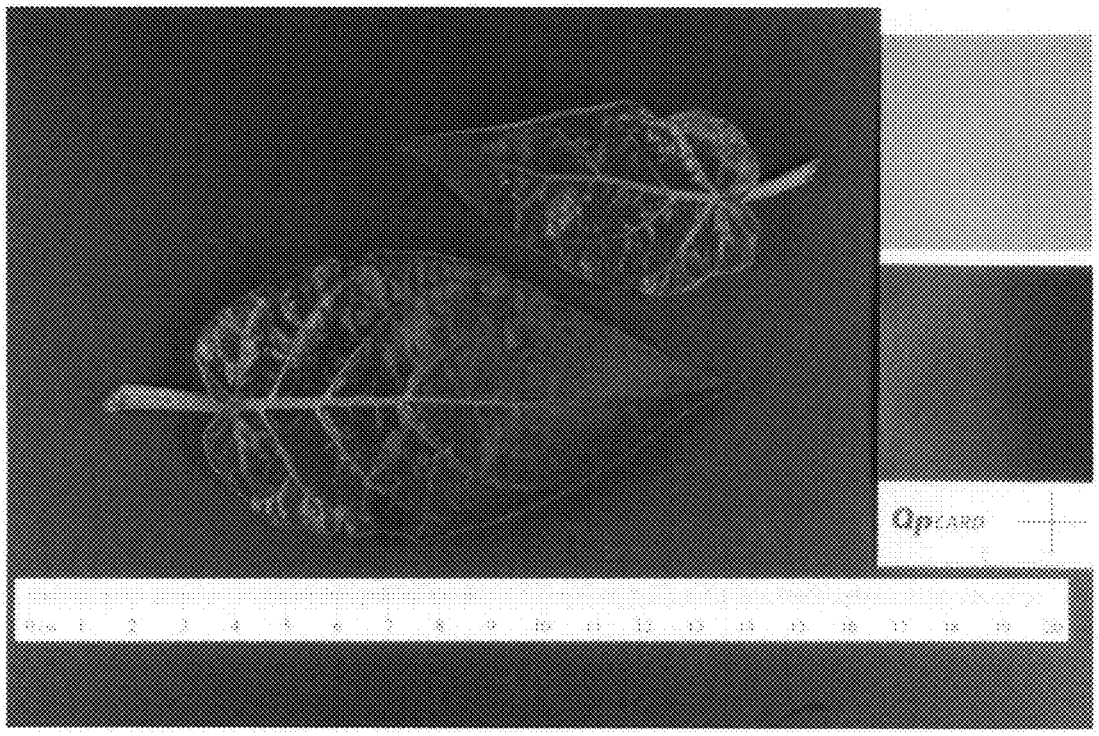
FIG. 5 shows examples of an immature leaf of the plant of the variety 'Sweeten'; view is of the upper surface of the leaves.
Figure 6:
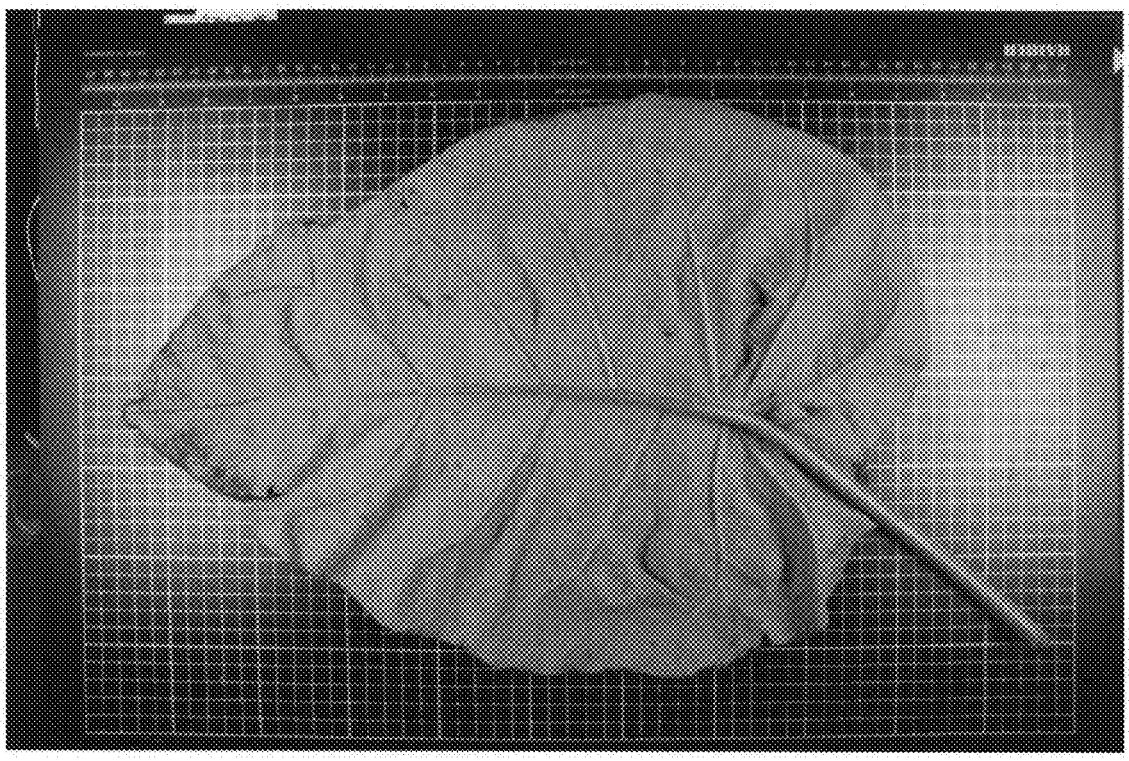
FIG. 6 shows an example of a mature leaf of the plant of the variety 'Sweeten'; view is of the lower surface of the leaf.
Figure 7:
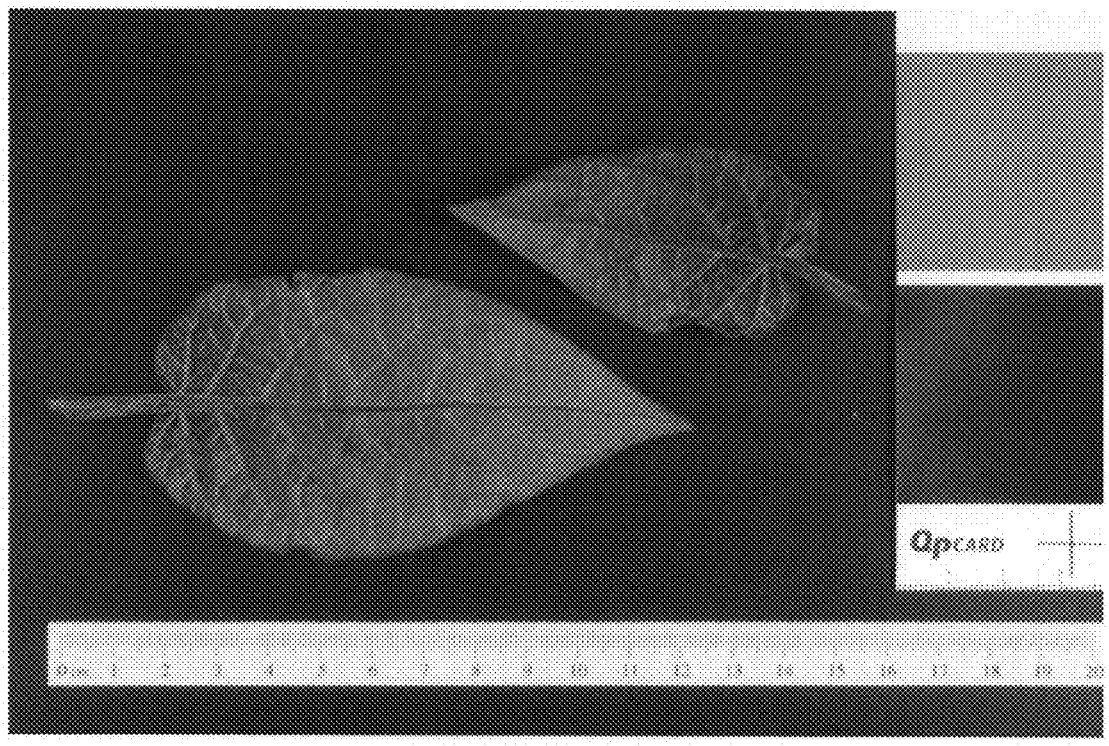
FIG. 7 shows examples of an immature leaf of the plant of the variety 'Sweeten'; view is of the lower surface of the leaves.
Figure 8:
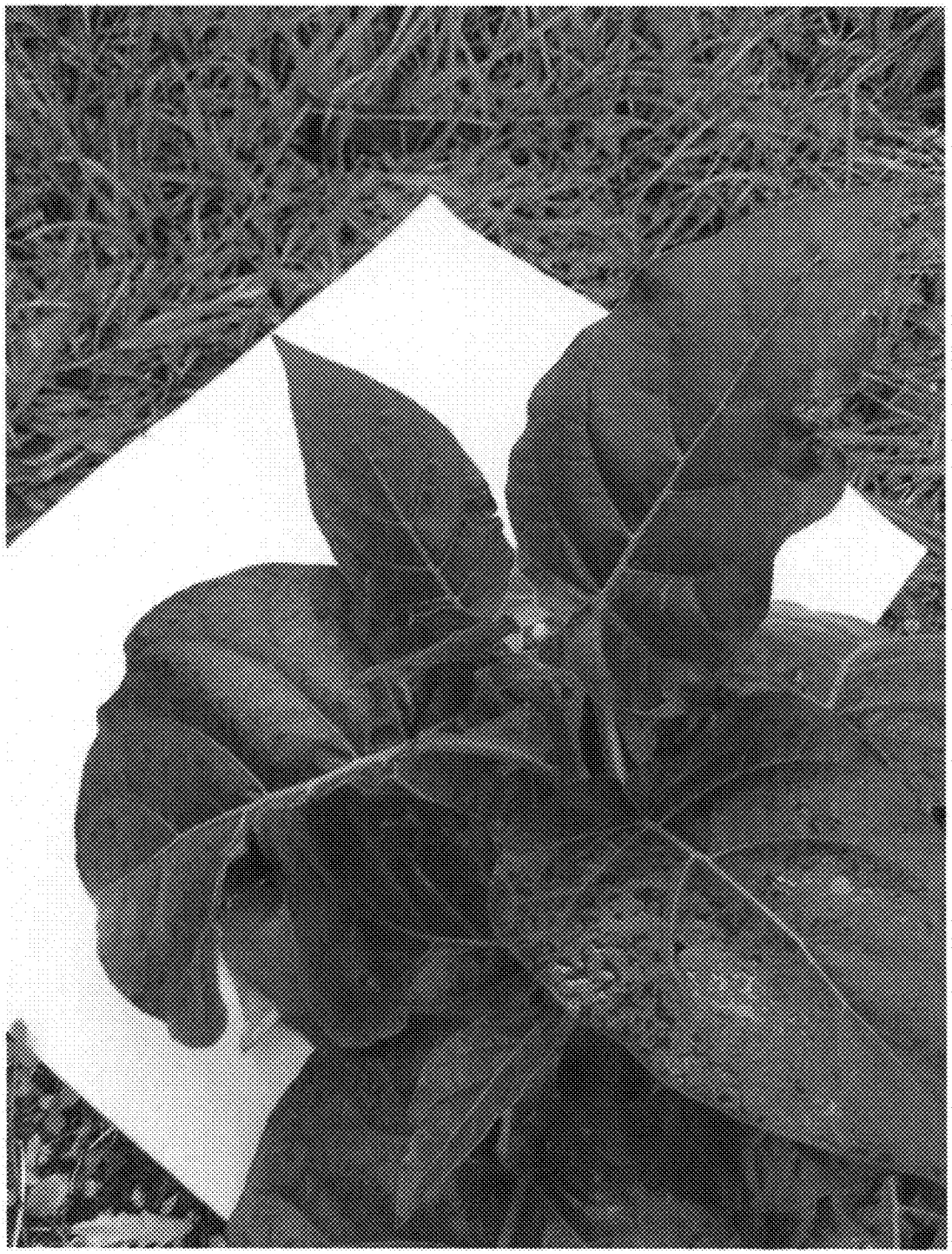
FIG. 8 shows examples of emerging immature leaves of the plant of the variety 'Sweeten'.

Leaves are overall large, ranging in dimension depending on the maturity of the individual; mature, fully expanded, leaf width averages in the range 225 mm to 322 mm, while length of the same leaves averages 330 mm to 440 mm (FIG. 4). Immature leaves, while appearing expanded are typically both shorter in length (around 160 mm) and less broad (around 110 mm) (FIG. 5). The leaves of the 'Sweeten' plant are arranged alternately. The leaves (both mature and immature) are cordate in shape, the bases of mature leaves are overlapping and the leaf tip is acuminate (FIGS. 4 and 5). The coloration of the upper surface of the leaf is green (near Green 137A), the under side being markedly lighter in color (near Green 138B) (FIGS. 4 and 6). Emerging leaves have strong anthocyanin coloration (near Red-purple 59A) (FIG. 8). The leaf margin is slightly undulate and on mature leaves some slight anthocyanin coloration is evident (near Red 53A) around the margin. A marked reticulate venation pattern is evident on the upper surface of the leaf as course veins, near Yellow-green 152B in color. The leaf surface is smooth overall although leaves can appear slightly wavy. When rubbed or brushed against the foliage gives off a distinctive musky smell, not uncommon among members of the Solanaceae family. The leaf stem of mature leaves ranges about 80 mm to 210 mm in length, while stems of immature leaves range about 40 mm to 110 mm in length. The diameter of mature leaf stems is about 11 mm while the diameter of immature leaf stems is about 6 mm. The leaf stems are variable in color, often darker towards the base (near Greyed-orange 177D) and lighter towards the base of the leaf blade (near Grey-brown 199C) although are predominantly green-flecked (near Greyed-green 194C). The flowers and fruit are borne on the previous year's growth. Flower buds typically arise about 10 mm to 15 mm from the base of 1 year old shoots.

Figure 9:
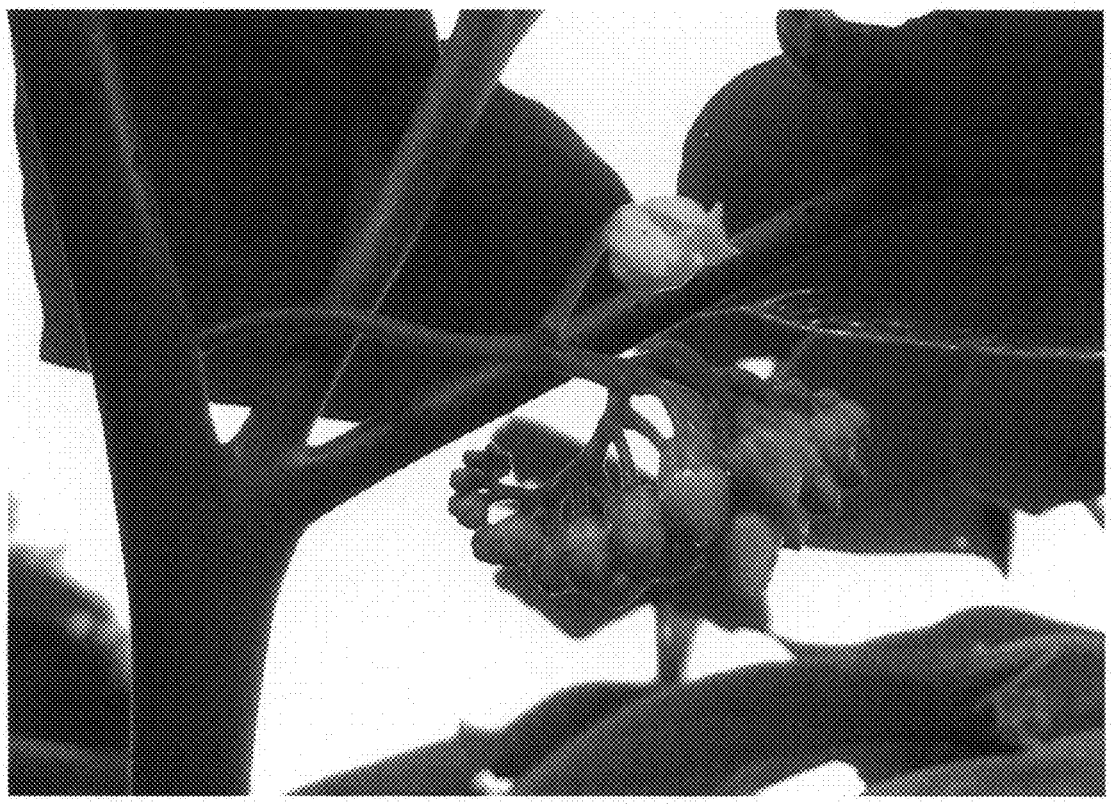
FIG. 9 shows the inflorescence of the plant of the variety 'Sweeten'.
Figure 10:
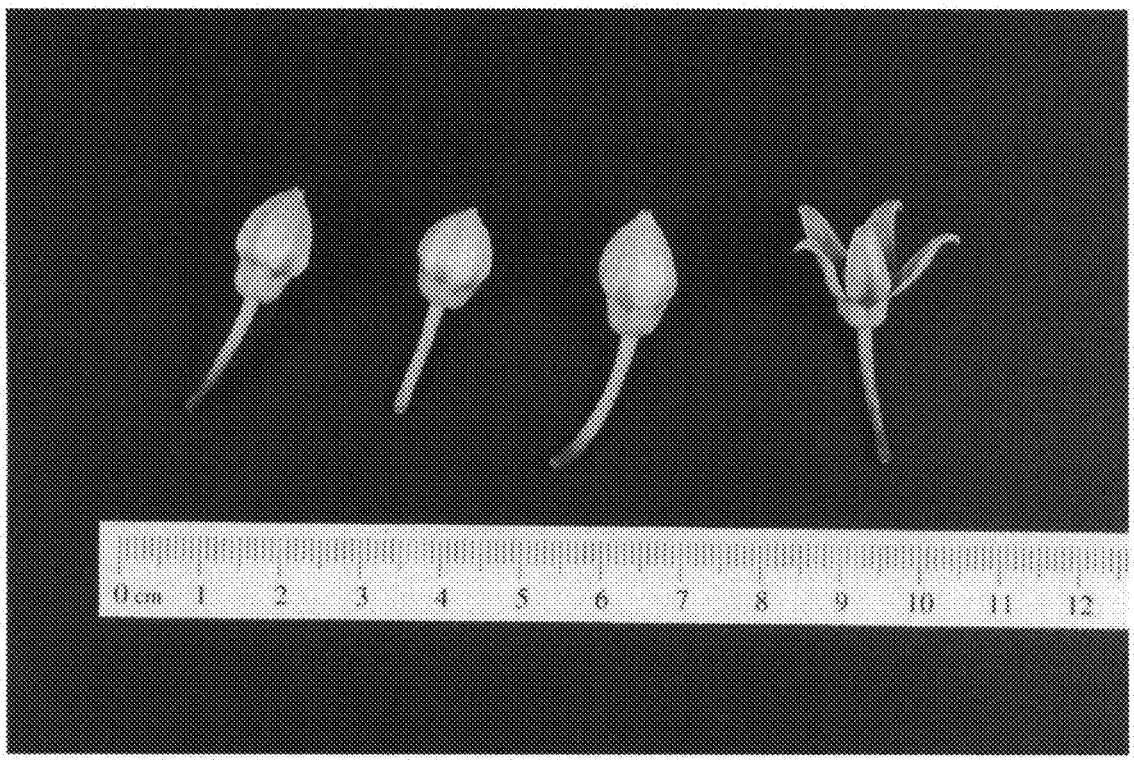
FIG. 10 shows buds and flowers of the plant of the variety 'Sweeten'.

Inflorescence: White flowers are borne on trusses (a multi-flowered inflorescence) (FIG. 9). Trusses are comprised of smooth, slender pedicels bearing multiple flower buds and flowers. The hierarchy of flower opening occurs from the bud nearest to the plant (most mature) to the tip of the truss (least mature); a truss may comprise flowers of different physiological maturity, from fully open flowers through to immature flower buds, at any one time. Flowering occurs over several weeks. A typical truss may carry in excess of 15 flowers. Each flower is rotate in form with five petals per flower (FIG. 10). The petal width is typically about 5 mm and about 8.5 mm in length. The petal tips are acuminate in shape, the tips curve back and under, and the petals are fused at the base. The average maximum width across the open flower is about 22.7 mm. The regular calyx is near Yellow-green 145C in color, as is the petiole. The petiole length of a mature flower averages about 16.24 mm and the diameter averages about 1.43 mm. An unopened bud is typically near Red 56D in color, and averages a maximum width of about 7.17 mm and 11.74 mm in length. The petiole of an unopened bud averages about 13.15 mm in length, and about 1.36 mm in diameter. Bright yellow pollen (near Yellow-orange 16A in color) is clearly visible within the open flowers. The flowers have no discernable fragrance. The plant is self fertile and is typically pollinated by bees. Un-pollinated flowers drop naturally.

Figure 11:
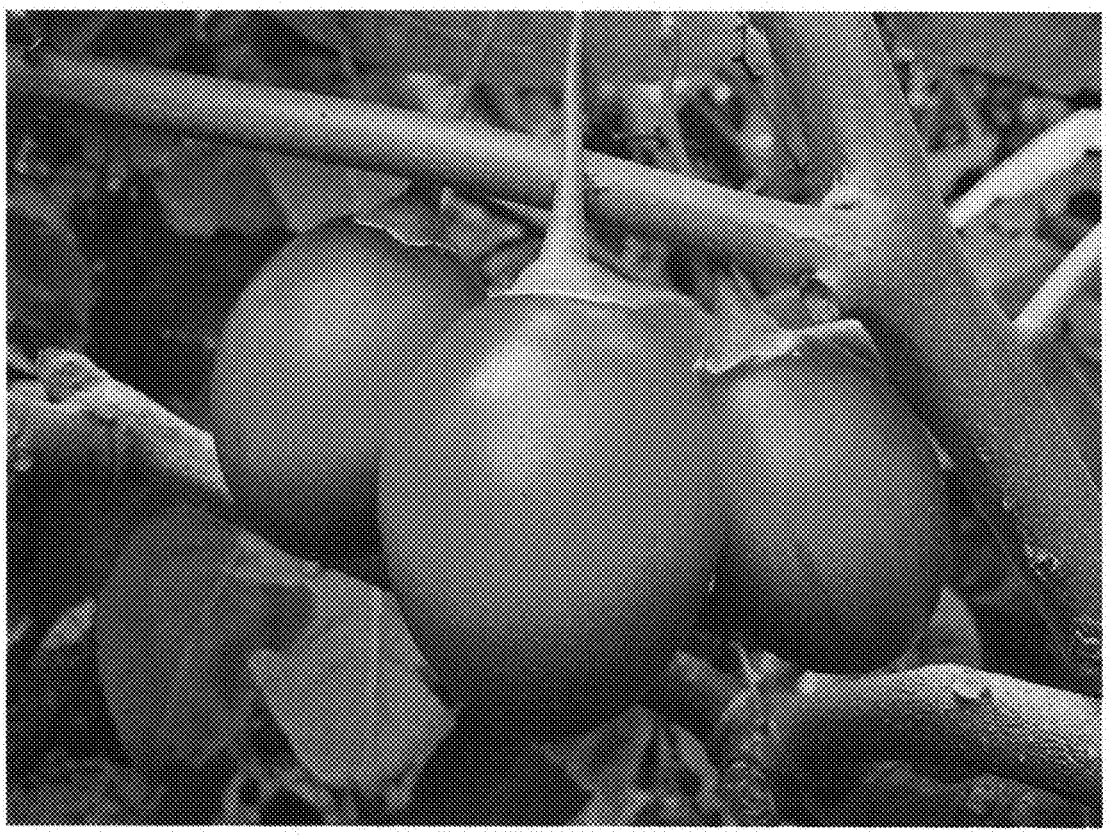
FIG. 11 shows fruit of the plant of the variety 'Sweeten' on the tree.
Figure 12:
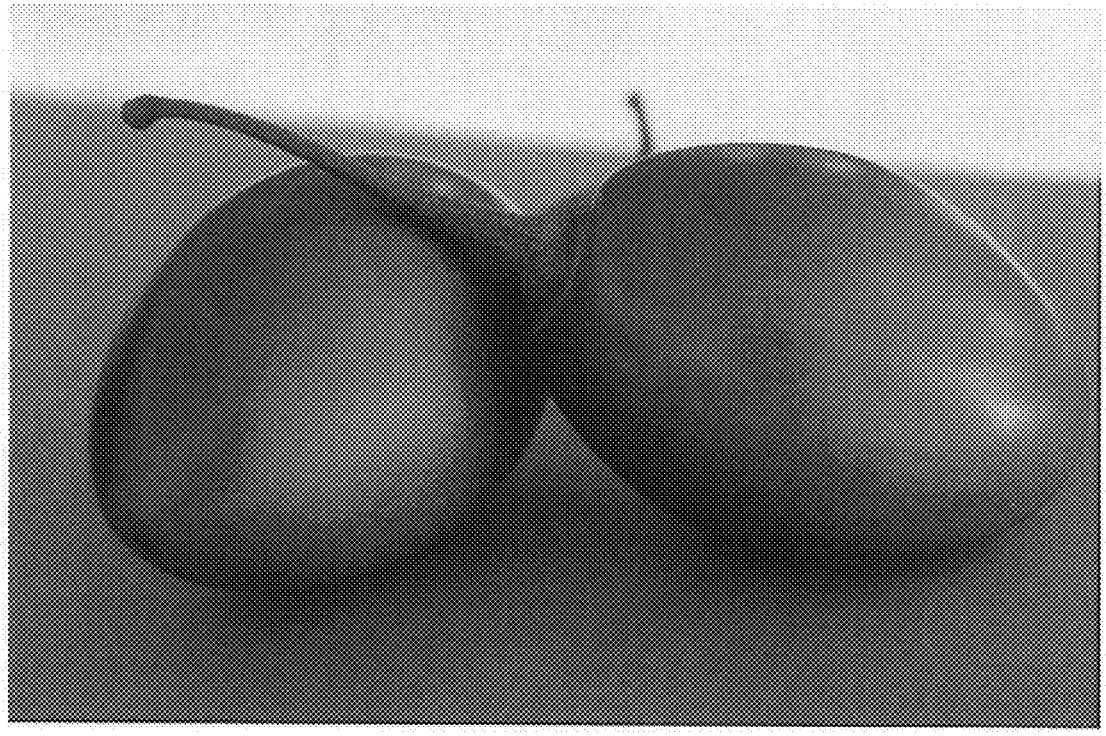
FIG. 12 shows fruit of the plant of the variety 'Sweeten' in the studio.
Figure 13:
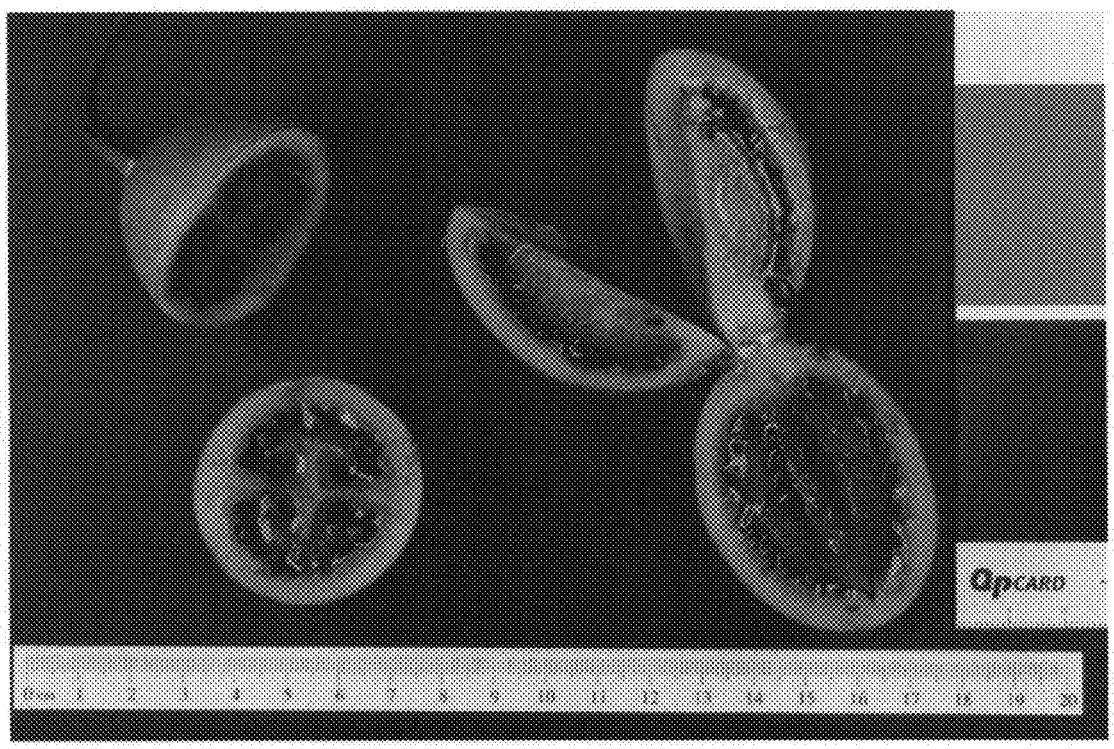
FIG. 13 shows fruit of the plant of the variety 'Sweeten'; view is of the cut surface in longitudinal and equatorial section.
Figure 14:
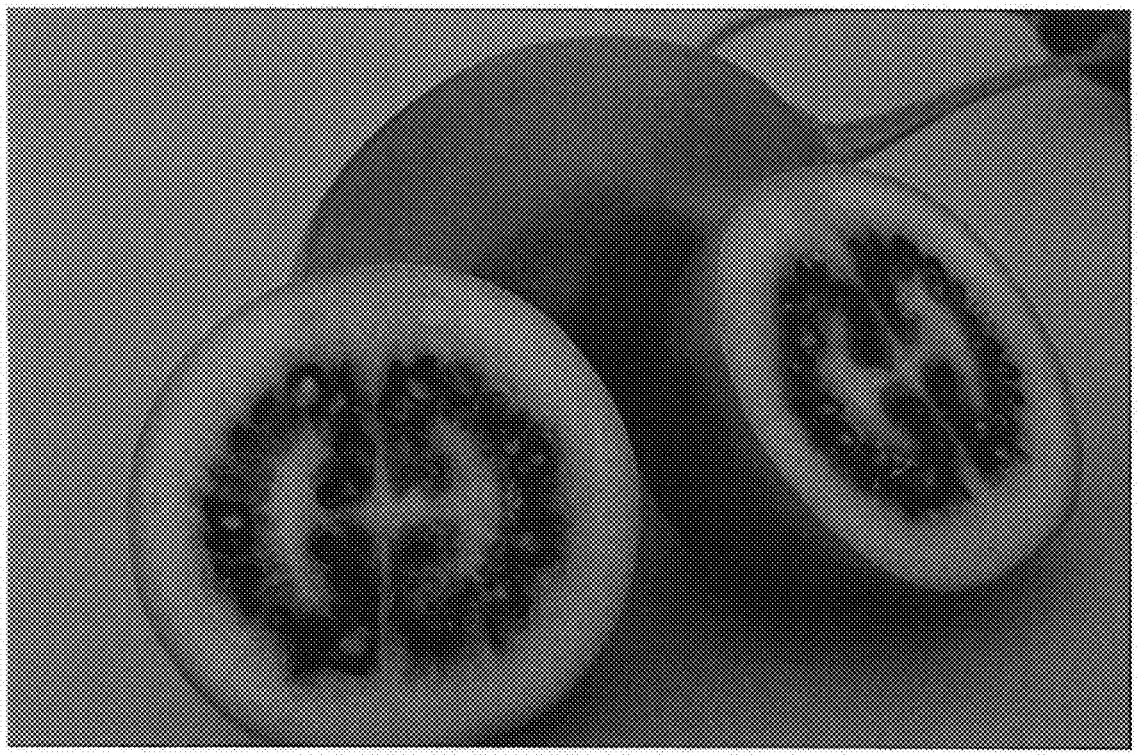
FIG. 14 shows fruit of the plant of the variety 'Sweeten'; view is of the whole fruit and the cut surface equatorial section.

Fruit: Fruit is typically borne singly, or in clusters of 3-12; fruit hang pendently in the tree (FIG. 11). The fruit is shiny, smooth-skinned and egg-shaped. Fruit shape is ovate in profile; on the basis of fruit length to width ratio, fruit is longer than broad. The shape of the fruit apex is rounded. The shape of fruit of 'Sweeten' differs from those of the unpatented variety 'Red Beau'; fruit of this variety being elliptic with a more pointed apex. Average fruit weight is approximately 66.5 g. On average fruit are about 60 mm long and 45.2 mm in diameter (at the widest point). Fruit size is related to seed content. Fruit size is achieved in about 15-17 weeks from fruit set Fruit color is orange-red; external color of immature fruit in the range near Green 138A to 138B, internal color near Green 145D. Deep red color (near Red 53B) develops as fruit reach harvest maturity (FIGS. 11 and 12). Faint darker, irregular longitudinal stripes are sometimes evident in the skin at full maturity (FIG. 11). The skin is tough, and is not edible, having a slightly resinous flavor. The calyx persists with the fruit. The fruit stem is near Yellow-green 144B in color when the fruit is ready to harvest. When cut the bright colored flesh and pulp is revealed (ranging near Orange 26B to 25A). When viewed in longitudinal section the fruit can be seen to be in a typical arrangement with seeds lodged within the pulpy endocarp surrounded in turn by the firmer flesh of the mesocarp. The central placenta and two longitudinal compartments containing the seeds and pulpy endocarp are evident in both the longitudinal and equatorial views of the cut fruit (FIG. 13). The flesh is sweet to sub-acid in flavor, more tangy than sugary. The internal flesh or pulp is firm but juicy, and contains many seeds like a tomato (FIG. 14). The seeds are overall black in color although the close association with the highly colored pulp and juice (near Greyed-purple 185B) gives the impression they are also somewhat colored. The seeds are nearly flat, round, and hard. On average the seeds are about 3.8 mm in diameter (at the widest point) and about 1.0 mm thick. The flesh, pulp, and seeds are edible. Soluble solids concentration of the juice from fruit at eating maturity is typically greater than 9° Brix. The cut surface of fruit does not brown readily. The juice will cause an indelible stain on cloth or other light surfaces. The seeds are near Greyed-purple 186B in color when dry. Seed numbers vary per fruit depending on growing conditions and the efficacy of pollination; the observed sample averaged about 280 seeds per fruit and total seed weighed on average about 2 g per fruit (when fresh).

Harvest and yield: Trees typically commence to crop within 18 months from planting. At physiological maturity, and under commercial production management, the annual yield per tree is about 20-30 kg. Fruits ripen progressively, and are harvested by selective hand picking of the most mature. Typically fruit reaches physiological maturity about 21 weeks from pollination. While fruit are overall firm, a slightly softening is detectible as fruit reach harvest maturity, and further softening occurs prior to being eating ready. The tough skin and firm flesh allow the fruit to be easily handled for post-harvest sorting and packing; the fruit also ships well, although storage life is short. Fruit commences ripening in early autumn (late March, early April) in Northland, New Zealand. Fruit continue to ripen and are able to be harvested through the autumn and winter months until spring (mid October). It is not uncommon for trees to bear immature and mature fruit as well as flowers, simultaneously.

Pest and disease resistance: Tamarillo trees are easily infected with tamarillo mosaic virus, which results in production of blotchy, streaked unattractive fruit, and, leaf mottling. Resistance to insect pests is unknown. The most common insect pest effecting tamarillo in New Zealand is Whitefly (most likely *Trialeurodes vaporariorum*).

Geographical adaptation: Observations indicate that the variety is suitable for warmer regions. 'Sweeten' performs well in the warm temperate climate of the Northland and Bay of Plenty regions, New Zealand. Based on this experience indications are that 'Sweeten' would also perform well in USDA plants hardiness zones 9-10 (published as the 2003 US National Arboretum "Web Version" of the USDA Plant Hardiness Zone Map USDA Miscellaneous Publication No. 1475, Issued January 1990).

Cultivation: Protection from wind is advisable as the plant is shallow-rooted and the branches somewhat brittle especially under full crop load. The plant does best in light, fertile soils, although is reputedly able to withstand some soil compaction. Drainage is essential as the plant does not withstand even short durations of water-logging. Annual pruning is advisable to encourage new shoot, and hence fruiting wood, development and to maintain light interception within the canopy. Left unmodified, internal shading within the canopy will result in fruiting occurring only on the outermost branches and tips. Under cultivation the tree can have a productive life up to about 10 years.

I claim:

1. A new and distinct tamarillo plant substantially as herein illustrated and described.

* * * * *